US00PP26170P3

(12) United States Plant Patent
Bédard

(10) Patent No.: US PP26,170 P3
(45) Date of Patent: Dec. 1, 2015

(54) GRANDIFLORA ROSE PLANT NAMED 'WEKSIRJUCI'

(50) Latin Name: *Rosa hybrida*
Varietal Denomination: WEKsirjuci

(71) Applicant: Early Morning LLC, Pomona, CA (US)

(72) Inventor: Christian Bédard, Placentia, CA (US)

(73) Assignee: Early Morning LLC, Pomona, CA (US)

( * ) Notice: Subject to any disclaimer, the term of this patent is extended or adjusted under 35 U.S.C. 154(b) by 236 days.

(21) Appl. No.: 13/998,529

(22) Filed: Nov. 7, 2013

(65) Prior Publication Data

US 2015/0128311 P1 May 7, 2015

(51) Int. Cl.
*A01H 5/02* (2006.01)

(52) U.S. Cl.
USPC ..... Plt./134

(58) Field of Classification Search
USPC ..... Plt./101, 130, 134
See application file for complete search history.

(56) References Cited

U.S. PATENT DOCUMENTS

PP18,473 P2 2/2008 Carruth
PP19,144 P2 8/2008 Carruth

*Primary Examiner* — Susan McCormick Ewoldt
*Assistant Examiner* — Karen Redden
(74) *Attorney, Agent, or Firm* — McKee, Voorhees & Sease, PLC

(57) ABSTRACT

A new variety of Grandiflora rose suitable for garden decoration, having flowers of even pure yellow coloration.

1 Drawing Sheet

Classification: The present invention relates to a new *Rosa hybrida* plant.

Variety denomination: The new plant has the varietal denomination 'WEKsirjuci'.

BACKGROUND OF THE INVENTION

This invention relates to a new and distinct variety of Grandiflora Rose. It has as its seed parent the variety known as 'WEKbepmey' (U.S. Plant Pat. No. 19,144) and as its pollen parent the variety known as 'WEKvossutono' (U.S. Plant Pat. No. 18,473).

SUMMARY OF THE INVENTION

Among the features which distinguish the new variety from other presently available and commercial rose cultivars known to the inventor are the following combinations of characteristics: its moderate fruity and spicy fragrance, its excellent color stability throughout the life of the flower and its large flower size for the class. The plant has a bushy moderately spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKsirjuci' may be asexually propagated by cuttings, budding and grafting. The budding and grafting successfully occurred on the plant/rootstock *Rosa hybrida* cv. Dr. Huey (not patented).

COMPARISON WITH PARENTS

The new rose may be distinguished from its seed parent, 'WEKbepmey' by the following combination of characteristics: whereas 'WEKsirjuci' bears somewhat large sized flowers (about 8.2 to about 12.1 cm. in diameter) of even pure yellow coloration, 'WEKbepmey' bears significantly smaller flowers (about 9.1 to about 10.7 cm. in diameter) of deep golden yellow coloration blushed with pink. The new variety has a bushy moderately spreading medium to somewhat tall growing habit (about 120 to about 170 cm. in height), whereas the seed parent has an upright significantly taller growing habit (about 160 to about 190 cm. in height).

The new variety may be distinguished from its pollen parent, 'WEKvossutono' by the following combination of characteristics: whereas 'WEKsirjuci' bears somewhat large sized flowers (about 8.2 to about 12.1 cm. in diameter) with double petalage (about 24 to 33 petals), 'WEKvossutono' bears significantly smaller flowers (about 5.7 to about 11.4 cm. in diameter) with heavier petalage (about 30 to 45 petals). The new variety has a bushy moderately spreading medium to somewhat tall growing habit (about 120 to about 170 cm. in height), whereas the pollen parent has a compact and bushy significantly shorter growing habit (about 70 to about 85 cm. in height).

COMPARISON WITH THE CLOSEST COMMERCIALLY AVAILABLE CULTIVAR

The new variety may be distinguished from its closest commercially available cultivar, 'WEKosomit' (U.S. Plant Pat. No. 14,401) by the following combination of characteristics: whereas 'WEKsirjuci' bears somewhat large sized flowers (about 8.2 to about 12.1 cm. in diameter) with double petalage (about 24 to 33 petals), 'WEKosomit' bears significantly larger flowers (about 9.7 to about 13.6 cm. in diameter) with heavier petalage (about 39 to 44 petals). The new variety has a bushy moderately spreading medium to somewhat tall growing habit (about 120 to about 170 cm. in height), whereas the closest commercially available cultivar has a bushy somewhat upright significantly taller growing habit (about 160 to about 210 cm. in height).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Pomona, Calif. in the month of November.

Throughout this specification, color references and/or values are based upon The Colour Chart of The Royal Horticultural Society (1966) except where common terms of color definition are employed.

DESCRIPTION OF THE NEW VARIETY

The following description is of 3 to 4 year-old rose plants of the new variety grown outdoors in Pomona, Calif. in the month of November. Phenotypic expression may vary with environmental, cultural and climatic conditions, as well as differences in conditions of light and soil.

FLOWER

The new variety usually bears its flowers singly, sometimes in clusters of two to three per stem. Flowers may be borne in regular rounded clusters on strong short to medium length stems (about 18 to about 60 cm.). Outdoors, the plant blooms abundantly and nearly continuously during the growing season. The flowers have a moderate fruity and spicy fragrance.

BUD

The peduncle is about 3.7 to about 5.4 cm. in length, of average caliper (about 0.2 to about 0.4 cm. in diameter), and usually erect. It is moderately rough, with some stipitate glands. Peduncle color is between 144A and 146A sometimes lightly suffused, especially on the side exposed to the sun, with between 183B and 187B.

Before the calyx breaks, the bud is about 1.1 to about 1.6 cm. in diameter at the widest point, about 1.6 to about 2.4 cm. in length, and pointed to somewhat ovoid in shape. The surface of the bud bears between 4 to 6 foliaceous appendages, some hairs and few stipitate glands, usually with slender entire foliaceous parts extending beyond the tip of the bud about ½ or more of its length. Bud color is between 137C and 146A.

The sepals are about 2.4 to about 4.9 cm. in length and about 0.9 to about 1.3 cm. in width at the widest point. The outer surface color of the sepal is between 137C and 146A. The outer surface of the sepal is mostly smooth and bears between 0 to 2 foliaceous appendages with few stipitate glands and some hairs. The inner surface color of the sepal is near 137C broadly bordered by near 137A. The inner surface of the sepal is covered with fine wooly tomentum; sepal margins are lined with some stipitate glands and many hairs.

The receptacle of the flower is of medium length (about 0.3 to about 0.7 cm.) and somewhat heavy in caliper (about 0.6 to about 1.1 cm. in diameter). The receptacle is cup-shaped in form. Its surface is smooth with thick fleshy walls. The receptacle color is between 144A and 146A.

As the petals open (after the calyx breaks), the bud is about 1.5 to about 3.1 cm. in diameter at the widest point, about 1.8 to about 3.3 cm. in length, and somewhat pointed to moderately ovoid in form. The color of the under surfaces of the newly opened petals is between 15B and 17B. There is no visible change in coloration at the point where the petal attaches. The color of the upper surfaces of the newly opened petals is between 14A and 17B. There is no visible change in coloration at the point where the petal attaches.

BLOOM

When fully open, the bloom ranges from about 8.2 to about 12.1 cm. in diameter. Petalage is double with about 24 to 33 petals and about 1 to 9 petaloids irregularly arranged. When partially open, the bloom form is moderately high centered to somewhat ovoid and slightly cupped, and the petals are moderately tightly spiraled to somewhat cupped and slightly undulated with petal edges somewhat reflexed outward. When fully open, the bloom form is cupped, and the petals are loosely cupped to moderately undulated with petal edges somewhat reflexed outward.

PETALS

The substance of the petals is moderately heavy and of medium to somewhat thick thickness, with upper surfaces moderately satiny and under surfaces matte to slightly shiny. The petals are about 3.6 to about 5.5 cm. in length and about 2.7 to about 5.8 cm. in width at the widest point. Petal margins are entire.

The outer petals are nearly round to somewhat obovate in shape with rounded apices and sometimes slightly notched with one notch.

The inner petals are obovate to somewhat oblanceolate in shape with rounded apices.

Petaloids are about 1.4 to about 4.3 cm. in length and about 0.8 to about 3.1 cm. in width at the widest point. Petaloids are irregularly shaped moderately obovate to somewhat oblanceolate with rounded apices.

NEWLY OPENED FLOWER

The under surface color of the outer, intermediate and inner petals is between 11B and 8A. There is no visible change in coloration at the point where the petal attaches. The upper surface color of the outer, intermediate and inner petals is between 10B and 9B. There is no visible change in coloration at the point where the petal attaches.

The under and upper surface colors of the petaloids are similar in coloration to the upper and under surfaces of the intermediate and inner petals.

The general tonality of the newly opened flower is between 10B and 9B.

THREE-DAY-OLD FLOWER

The under and upper surface color of the outer, intermediate and inner petals is between 11B and 10C. There is no visible change in coloration at the point where the petal attaches.

The under and upper surface colors of the petaloids are similar in coloration to the upper and under surfaces of the intermediate and inner petals.

The general tonality of the three-day-old flower is between 11B and 10C.

On the spent bloom, the petals usually drop off cleanly.

In November in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 95) and are arranged regularly about the pistils; a few are mixed with petaloids. The filaments are of medium to somewhat long length (about 0.4 to about 1.4 cm.) most with anthers. Filaments are between 14A and 13A in color. The anthers are of medium size for the class and all open approximately at the same time. Anther color when immature is near 22A on the external part and near 10D on the internal part. Anther color at maturity is near 164B on the external part and near 200A on the internal part. Pollen is abundant and between 21B and 17B in color.

FEMALE REPRODUCTIVE ORGANS

Pistils vary in number (average about 80). The styles are moderately even, average in length (about 0.4 to about 0.8 cm.), somewhat thin in caliper, and loosely bunched to somewhat separated. Stigma color is between 13B and 12A. Style color is between 2D and 4D often lightly suffused with between 53B and 53C. Ovaries are usually all enclosed in the calyx.

Hips are moderately long in length (about 2.0 to about 2.5 cm.), rounded in form with a flat top, and between 28A and 28B in color when ripe. The hip surface is smooth with thick fleshy walls. The sepals are somewhat permanent, and usually straight in shape.

The seeds are irregularly rounded, smooth in texture, approximately 24 to about 30 per hip, about 0.3 to about 0.8 cm. in diameter at the widest point and between 164D and 165D in color.

FOLIAGE

The compound leaves are usually comprised of three to seven leaflets and are borne abundantly. The five-leaflet leaves are about 9.5 to about 12.1 cm. in length and about 7.8 to about 11.2 cm. in width at the widest point, moderately leathery to somewhat crisp in texture, and glossy in finish on the upper side and matte in finish on the under side. The leaves have a pinnate venation pattern. The terminal leaflets are about 4.8 to about 7.8 cm. in length and about 3.0 to about 4.1 cm. in width at the widest point, shaped oval to somewhat lanceolate with acute apices and rounded to somewhat acute bases. Their margins are usually simply serrate.

The upper surface color of the mature leaf is between 137A and 147A. The under surface color of the mature leaf is between 147B and 146B. The under and upper colors of the leaf veins on the mature leaf are similar in coloration to the upper and under surfaces colors of the mature leaf. The upper surface color of the young leaf is between 146B and 137C, often lightly suffused with between 187B and 178A. The under surface color of the young leaf is between 146B and 137C, often moderately suffused with between 187B and 178A. The under and upper colors of the leaf veins on the young leaf are similar in coloration to the upper and under surfaces colors of the young leaf.

The rachis is somewhat light in caliper and mostly smooth. The upper side is shallowly grooved with some hairs and few stipitate glands on the edges of the grooves. The under side of the rachis is mostly smooth with occasionally few small prickles. The rachis color is near 146C on the under side and near 137C on the upper side.

The stipules are about 0.9 to about 1.2 cm. in length and of medium width (about 0.4 to about 0.8 cm.) with medium length straight points that usually turn out at an angle of more than 45 degrees and sometimes recurve toward the stem. The under and upper surface color of the stipule is between 138A and 146B.

The petiole is somewhat light in caliper and smooth. The upper side is shallowly grooved with some hairs and few stipitate glands on the edges of the grooves. The under side of the petiole is smooth. The petiole is about 0.3 to about 1.4 cm. in length and about 0.1 to about 0.2 cm in width at the widest point. The petiole color is near 146C on the under side and near 137C on the upper side.

The plant displays an above average degree of resistance to powdery mildew and rust as compared to other commercial varieties grown under comparable conditions in Pomona, Calif. The plant's winter hardiness and drought/heat tolerance are yet to be determined.

GROWTH

The plant has a bushy moderately spreading medium to somewhat tall growing habit (about 120 to about 170 cm. in height and about 150 to about 200 cm. spread at the widest point), with very full branching. It displays vigorous growth and the canes are of somewhat heavy caliper for the class (about 1.7 to about 2.9 cm. in diameter at the widest point).

The color of the major stems is between 147B and 146A. They bear some large prickles that are about 0.6 to about 1.0 cm. in length. The large prickles are almost straight and angled slightly downward with a somewhat short broad to oval base; prickle color is between 165B and 164A. The major stem bears few small prickles of similar shape and coloration.

The color of the branches is between 146B and 137C. They bear few large prickles which are of similar size and shape to the large prickles on the major stems; prickle color is between 160A and 162B. The branches bear few small prickles of similar shape and coloration.

The color of the new shoots is between 144B and 147A sometimes moderately suffused with between 187B and 178A. They bear few large prickles which are of similar size and shape to the large prickles on the major stems; prickle color is between 151A and 153A often moderately suffused with between 187B and 187C. The shoots bear few small prickles of similar shape and coloration.

I claim:

1. A new and distinct Grandiflora rose plant of the variety substantially as described and illustrated herein.

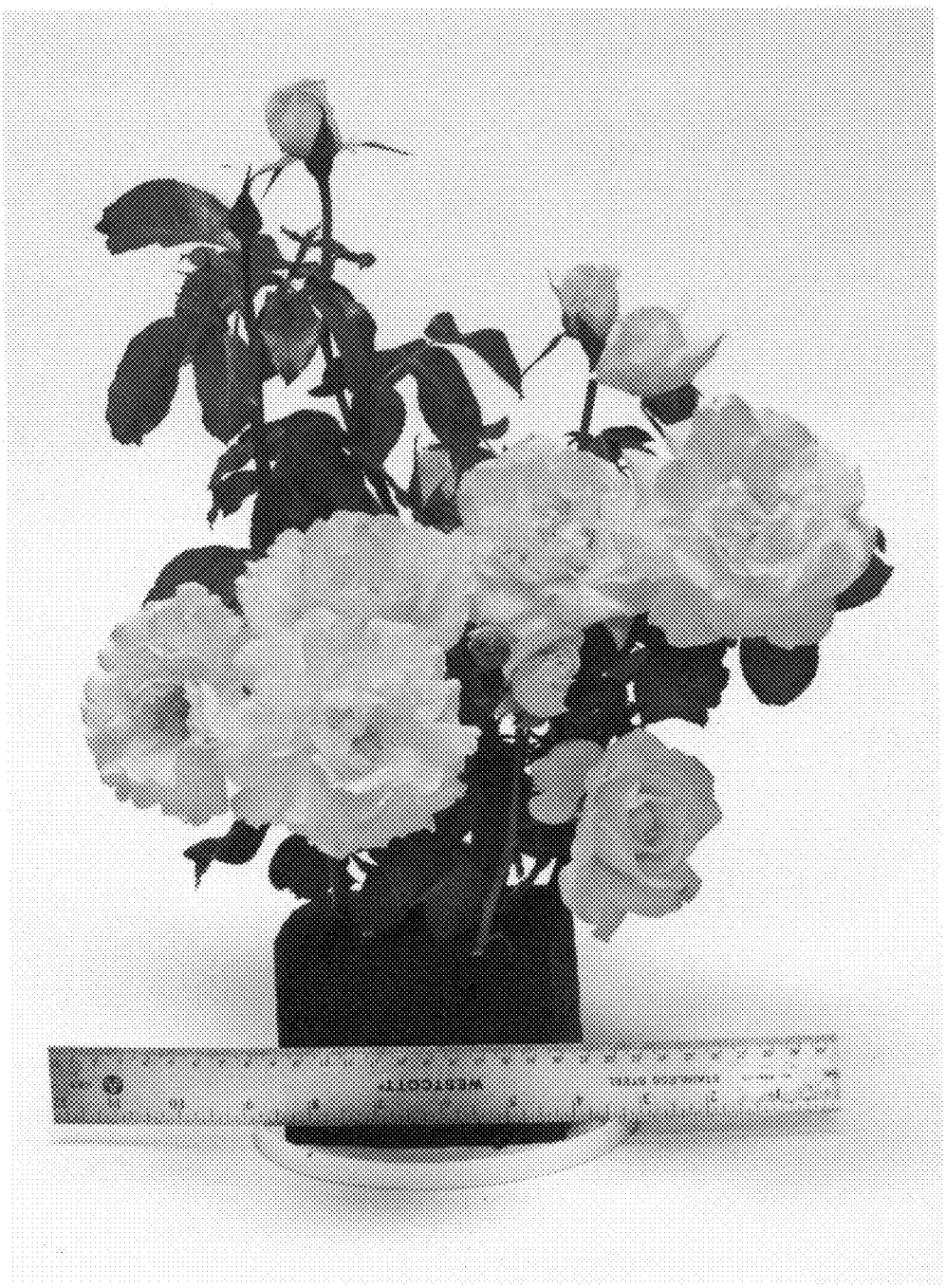

* * * * *